Sept. 21, 1948. P. MORDIGAN Plant Pat. 806
ROSE PLANT
Filed Feb. 26, 1947
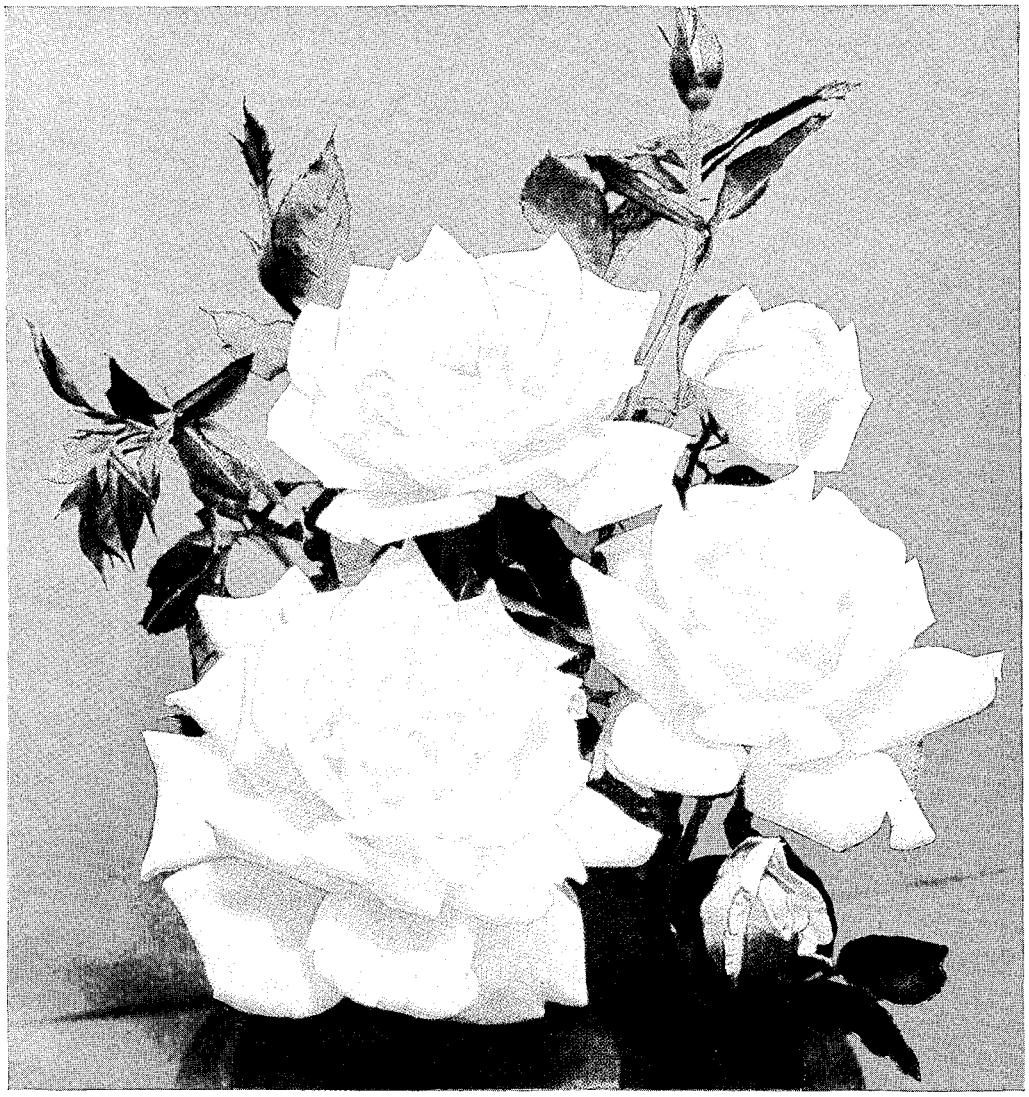
Inventor
Peter Mordigian
by Robb & Robb
attorneys Patented Sept. 21, 1948

Plant Pat. 806

UNITED STATES PATENT OFFICE

806

ROSE PLANT

Peter Mordigan, San Fernando, Calif., assignor to The Conard-Pyle Company, West Grove, Pa., a corporation of Pennsylvania Application February 26, 1947, Serial No. 731,022

1 Claim. (Cl. 47—61)

The present discovery relates to a new and distinct variety of hybrid tea rose plant, originating as a sport of the variety "Good News" (Pl. Pat. #426).

This new variety is characterized as to novelty by the new color of its flowers, distinguished materially from that of its parent and rare in any yellow rose, and, as such, constituting an excellent yellow flower on an unusually vigorous, well branched and well foliaged plant.

Asexual reproduction shows that these characteristics hold true through succeeding propagations.

The accompanying drawing illustrates specimens of the flowers of this new rose in the various stages of development from bud to full blown blooms.

The following is a detailed description of the new variety, all reference to color being in accord with Ridgway's Color Standard:

Breeding: Sport.
*Parent.*—"Good News."
Type: Hardy; bush; outdoor; sport; for cut flowers and garden decoration.
Class: Hybrid tea.

*Flower*

Locality where grown: West Grove, Pennsylvania.
Flowers borne: Singly to stem; on strong, medium long stems.
Quantity of bloom: Free; outdoors.
Continuity: Continuous.
Fragrance: Strong; tea.
Bud:
*Peduncle.*—Medium length; erect; Light Cress Green, Plate XXXI; numerous Morocco Red, Plate I, prickles.
*Before calyx breaks.*—Size—medium. Form—ovoid with a conspicuous neck; with foliaceous appendages on the surface of the bud; with foliaceous parts extending beyond the tip of the bud equal to ¾ or more of its length.
*As calyx breaks.*—Color—Brazil-Red, Plate I, and Capucine Orange, Plate III.
*As first petal opens.*—Size—medium. Form—ovoid. Color—outside: Capucine-Orange, Plate III; inside: Apricot-Yellow, to Baryta Yellow, Plate IV.
*Opening.*—Opens up well.
Bloom:
*Size.*—When fully open—large; 4½ inches to 5 inches.
*Petalage.*—Very double; from 50 to 60 petals; arranged regularly.

*Form.*—Full high center; remaining high centered; petals remaining at first rolled outward; becoming later, loosely rolled outward.
Petals: Thick; soft; with inside and outside satiny.
*Shape.*—Outside—obovate; scalloped with 1 notch; intermediate — obovate; inside — obovate.

This description of a newly opened flower was made from a rose grown outdoors, in the month of September, at West Grove, Pennsylvania:

*Color.*—*Outside petal*—outside surface: Capucine-Orange, to Pale Yellow Orange, Plate IV; inside surface: Light Cadmium, Plate IV, to Orange-Buff, Plate III. *Intermediate petal*—outside surface: Ochraceous-Salmon, Plate XV; inside surface: Antimony-Yellow, Plate XV. *Inner petal*—outside surface: Ochraceous-Salmon, Plate XV; inside surface: Antimony-Yellow, Plate XV.

This description was made from a rose that was open for three days outdoors, in the month of September, at West Grove, Pennsylvania:

*Outside petal.*—Outside surface: Capucine-Buff, Plate III, to White; inside surface: Antimony-Yellow, Plate XV, to White. *Inside petal.*—Outside surface: Pinard Yellow, Plate IV; inside surface: Pinard Yellow, Plate IV.
*General color effect.*—Newly opened flower—Cadmium-Yellow, Plate III. Three days open—Orange-Buff, Plate III.
*Behavior.*—Persist; fading Ivory Yellow, Plate XXX.
*Flower longevity.*—On bush in garden, 5 days, in September. Cut roses grown outdoors kept at living room temperatures, 3 to 4 days in September.

*Reproductive organs*

Stamens: Many; arranged irregularly about pistils.
Filaments: Medium length; Lemon-Chrome, Plate IV; most with anthers.
Anthers: Medium size; Deep-Chrome, Plate III; open at various times.
Pollen: Sparse; Pale Orange Yellow, Plate III.
Pistils: Many.
Styles: Long; thin; columnar.
Stigma: Rose Doree, Plate I.
Ovaries: All enclosed in calyx.

Hips: Ovoid; neck pear-shaped; Parrot Green, Plate VI; walls, thick, fleshy.

Sepals: Permanent; moderately long; spear-shaped; recurved.

Seeds: Few; medium large.

*Plant*

Foliage:

*Leaves.*—Compound of 5 to 7 leaflets; normal; moderately large; leathery.

*Leaflets.*—Oval with apex acute; base round; margin simply serrate.

*Color.*—Mature—upper surface: Dark Cress Green, Plate XXXI; under surface: Light Cress Green, Plate XXXI. *Young*—upper surface: Claret Brown, Plate I; under surface: Garnet Brown, Plate I.

*Rachis.*—Medium heavy. Upper side: smooth; grooved; under side: smooth.

*Stipules.*—Medium length; narrow; with moderately long points, turning out at an angle of less than 45°.

*Disease.*—Resistant to mildew and blackspot.

Growth:

*Habit.*—Bushy; upright; much branched.

*Growth.*—Vigorous.

*Canes.*—Moderately heavy.

*Main stems.*—Dull; Cerro Green, Plate V. *Thorns*—several; medium length; hooked downward; with broad base. *Prickles and hairs*—none.

*Branches.*—Dull; Cerro Green, Plate V. *Thorns*—several; medium length; hooked downward; with broad base. *Prickles and hairs*—none.

*New shoots.*—Citrine, Plate IV. *Thorns*—several; hooked downward; with narrow base. *Prickles and hairs*—none.

I claim:

A new and distinct variety of hybrid tea rose plant characterized as to novelty by the extremely rare yellow color of its flowers on an unusually vigorous, well branched and well foliaged plant, substantially as shown and described.

PETER MORDIGAN.